(12) United States Patent
Liu et al.

(10) Patent No.: US 9,695,299 B1
(45) Date of Patent: Jul. 4, 2017

(54) PHOSPHOROUS-CONTAINING COMPOUND, APPLICATION THEREOF, AND METHOD FOR PREPARING THE SAME

(71) Applicant: National Tsing Hua University, Hsinchu (TW)

(72) Inventors: Ying-Ling Liu, Hsinchu (TW); Chih-Yuan Hsu, Kaohsiung (TW)

(73) Assignee: National Tsing Hua University, Hsinchu (TW)

( * ) Notice: Subject to any disclaimer, the term of this patent is extended or adjusted under 35 U.S.C. 154(b) by 19 days.

(21) Appl. No.: 15/135,802

(22) Filed: Apr. 22, 2016

(30) Foreign Application Priority Data

Dec. 29, 2015 (TW) .............................. 104144142 A

(51) Int. Cl.
*C09K 21/12* (2006.01)
*C08K 5/53* (2006.01)
(Continued)

(52) U.S. Cl.
CPC .......... *C08K 5/53* (2013.01); *C07F 9/657163* (2013.01); *C08G 79/04* (2013.01)

(58) Field of Classification Search
None
See application file for complete search history.

(56) References Cited

U.S. PATENT DOCUMENTS 8,512,466 B2 * 8/2013 Hayashi .................. C07F 9/306
106/310
8,962,773 B2 2/2015 Gan

OTHER PUBLICATIONS

STN Structure Search Results (Jan. 23, 2017).*

* cited by examiner

*Primary Examiner* — Vu A Nguyen
(74) *Attorney, Agent, or Firm* — Brinks Gilson & Lione; John C. Bacoch

(57) ABSTRACT

A phosphorous-containing compound is represented by Formula (I):

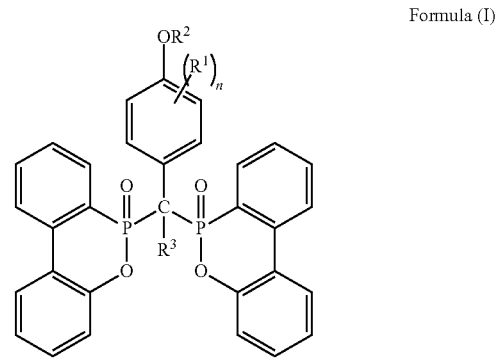

Formula (I)

wherein
n is an integer ranging from 1 to 4;
$R^1$ represents hydrogen or a linear or branched $C_1$-$C_4$ alkyl group, and a plurality of $R^1$s are the same or different when n is larger than 1;
$R^2$ represents hydrogen, or (Continued)

wherein Ep is an epoxy resin moiety; or
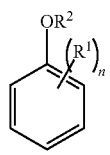
represents
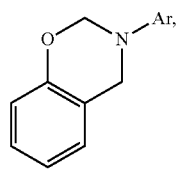
wherein Ar represents a linear or branched $C_1$-$C_{12}$ alkyl group or a $C_6$-$C_{12}$ aryl group; and
$R^3$ represents hydrogen or methyl.
10 Claims, 2 Drawing Sheets
(51) Int. Cl.
*C07F 9/6571* (2006.01)
*C08G 79/04* (2006.01)

PHOSPHOROUS-CONTAINING COMPOUND, APPLICATION THEREOF, AND METHOD FOR PREPARING THE SAME

CROSS-REFERENCE TO RELATED APPLICATION

This application claims priority of Taiwanese Application No. 104144142, filed on Dec. 29, 2015.

FIELD

The disclosure relates to a phosphorous-containing compound, and more particularly to a phosphorous-containing compound used as a reactive type flame retardant for resins such as epoxy resins and phenolic resins. The disclosure also relates to an application of the phosphorous-containing compound and a method for preparing the phosphorous-containing compound.

BACKGROUND

Halide compounds are conventionally used as flame retardants for imparting polymeric materials, such as epoxy resins and phenolic resins, with a flame-retardant property. However, to meet the requirements for environmental protection, the flame retardants for flame-retardant polymeric materials are required to be halogen-free. The flame retardants commonly used on the market are phosphorous-based flame retardants, such as phosphates and phosphonates. However, the phosphorous-based flame retardants usually have problems of inferior thermal stability and hydrolysis resistance. In order to solve the problems, various derivatives from 9,10-dihydro-9-oxa-10-phosphaphenanthrene-10-oxide (referred to as DOPO hereinafter) have been developed.

In addition, in order to be useful in electronic materials of thermoset resins, the flame retardants should have a chemical group reactive with the thermoset resins, i.e., of the reactive type.

TW 572954 discloses a reactive type phosphorous-containing flame retardant having a chemical structure represented by

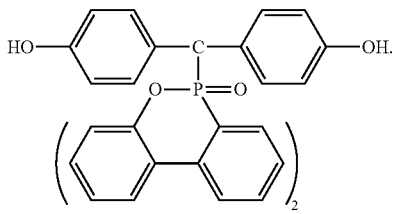

As shown in the chemical structure, the reactive type phosphorous-containing flame retardant disclosed in TW 572954 contains two phenyl groups each having a reactive group (i.e., OH) and two DOPO moieties. The phosphorous content of the reactive type phosphorous-containing flame retardant is merely 9.86 wt %. It should be noted that the flame-retardant effect of the reactive type phosphorous-containing flame retardant is directly proportional to the phosphorous content of the reactive type phosphorous-containing flame retardant.

U.S. Pat. No. 8,962,773 B2 discloses two reactive type phosphorous-containing flame retardants having chemical structures respectively represented by

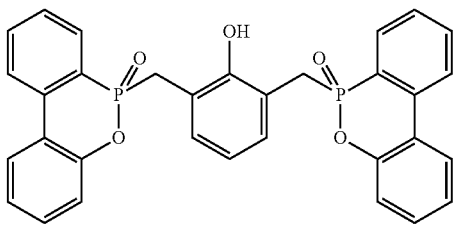 [SMILES: O=P1(Cc2cccc(CP3(=O)Oc4ccccc4-c4ccccc43)c2O)Oc2ccccc2-c2ccccc21]

and

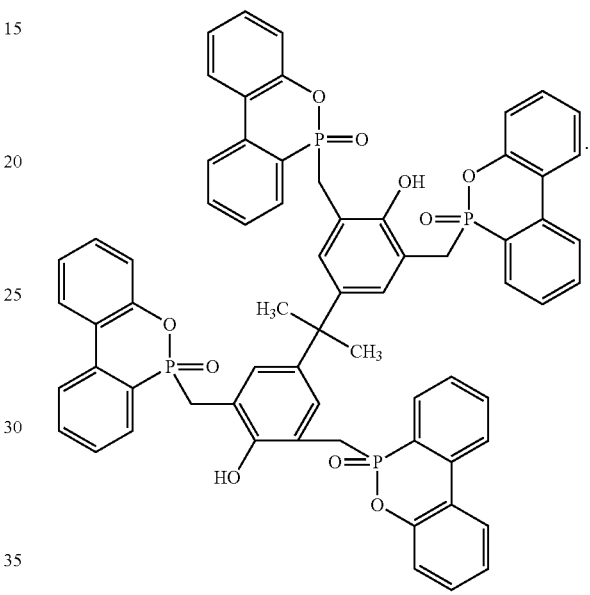

Although the phosphorous contents of these two reactive type phosphorous-containing flame retardants are relatively high, 11.25 wt % and 10.86 wt %, respectively, compared to the reactive type phosphorous-containing flame retardant disclosed in TW 572954, the reactants for synthesizing them are not readily available. In addition, as shown in the two chemical structures above, the DOPO moiety is at an ortho position to the reactive —OH group, which may cause steric hindrance to the subsequent reaction of the reactive —OH group so that the reactivity of these two reactive type phosphorous-containing flame retardants may be relatively reduced.

U.S. Pat. No. 8,512,466 B2 discloses a phosphorous-containing oligomer useful as a reactive type flame retardant and having a chemical structure represented by

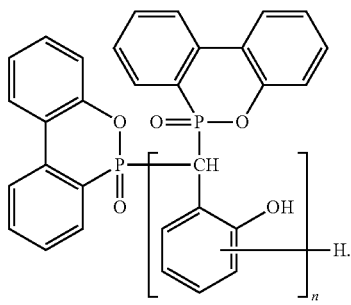

3

As shown in the chemical structure, the phosphorous-containing oligomer has a number n (n≥1) of phenyl groups each having a reactive group (i.e., OH), and a number n+1 of DOPO moieties. That is, the phosphorous-containing oligomer is not a pure compound. In addition, the phosphorous-containing oligomer is obtained by conducting two stages of reactions, i.e., a reaction at 80° C. to 180° C., followed by a reaction at 120° C. to 200° C.

U.S. Pat. No. 8,648,154 B2 discloses a phosphorous-containing phenol novolac resin prepared by subjecting 4-hydroxybenzaldehyde and DOPO to a reaction (Reaction 1) to produce DOPO-HB, and subjecting DOPO-HB and an aldehyde to a further reaction (Reaction 2).

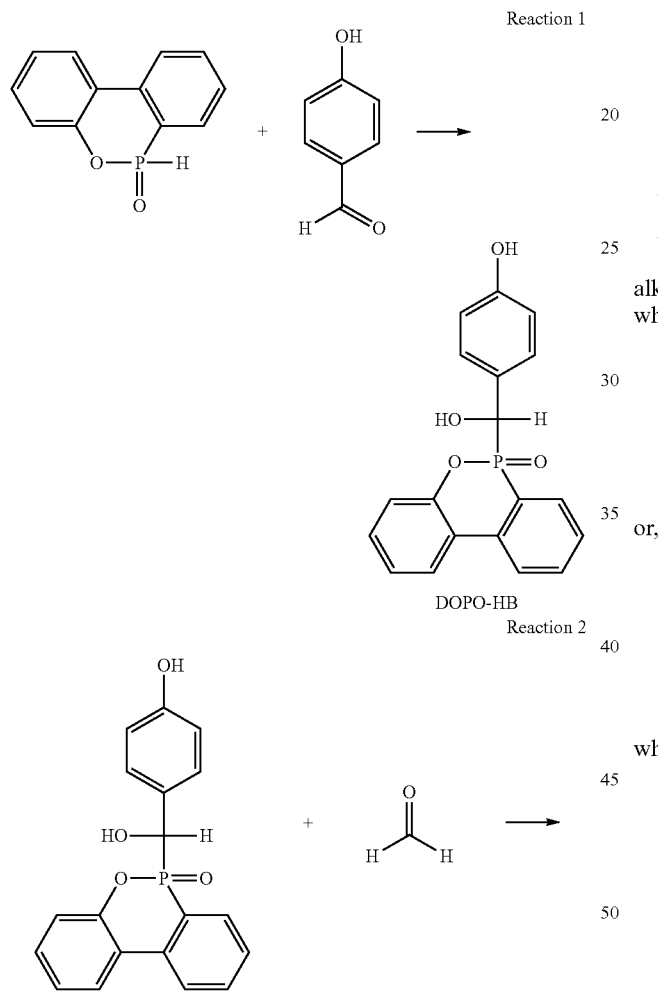

SUMMARY

A first object of the disclosure is to provide a phosphorous-containing compound which is useful as a reactive type flame retardant for resins so as to enhance the flame retardance and thermal stability of the resins.

A second object of the disclosure is to provide a flame-retardant resin composition containing the phosphorous-containing compound.

A third object of the disclosure is to provide a cured flame-retardant resin obtained by curing the flame-retardant resin composition.

4

A fourth object of the disclosure is to provide a method for preparing the phosphorous-containing compound.

According to a first aspect of the disclosure, there is provided a phosphorous-containing compound represented by Formula (I):

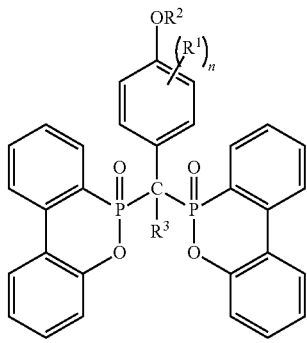

Formula (I)

wherein n is an integer ranging from 1 to 4;

$R^1$ represents hydrogen or a linear or branched $C_1$-$C_4$ alkyl group, and a plurality of $R^1$s are the same or different when n is larger than 1;

$R^2$ represents hydrogen,

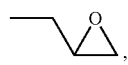, or,

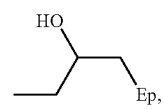

wherein Ep is an epoxy resin moiety; or

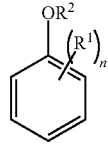

represents

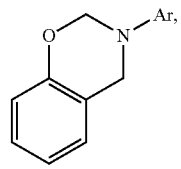

wherein Ar represents a linear or branched $C_1$-$C_{12}$ alkyl group or a $C_6$-$C_{12}$ aryl group; and $R^3$ represents hydrogen or methyl.

According to a second aspect of the disclosure, there is provided a flame-retardant resin composition which includes the phosphorous-containing compound and a resin.

According to a third aspect of the disclosure, there is provided a cured flame-retardant resin obtained by curing the flame-retardant resin composition.

According to a fourth aspect of the disclosure, there is provided a method for preparing the phosphorous-containing compound. The method includes the step of:

subjecting a p-hydroxy benzoyl derivative of Formula (II) and an oxa-phosphaphenanthrene oxide of Formula (III) to a reaction at a temperature ranging from 190 to 250° C. in the absence of a solvent, Formula (II)

Formula (III)

wherein
n, $R^1$ and $R^3$ are the same as those defined for the phosphorous-containing compound represented by Formula (I), and a molar ratio of the p-hydroxy benzoyl derivative to the oxa-phosphaphenanthrene oxide ranges from 1:2 to 1:5.5.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

The phosphorous-containing compound of the disclosure is represented by Formula (I):

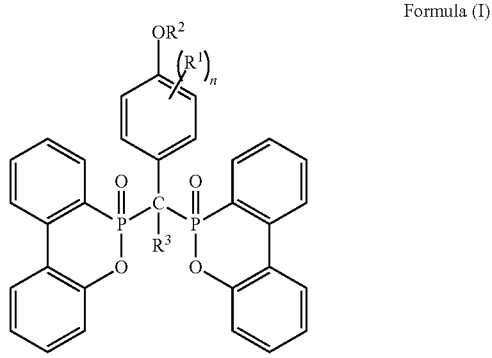

Formula (I)

wherein
n is an integer ranging from 1 to 4;
$R^1$ represents hydrogen or a linear or branched $C_1$-$C_4$ alkyl group, and a plurality of $R^1$s are the same or different when n is larger than 1;
$R^2$ represents hydrogen,

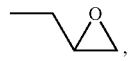

or

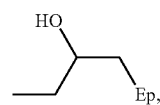

wherein Ep is an epoxy resin moiety; or

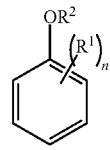

represents wherein Ar represents a linear or branched $C_1$-$C_{12}$ alkyl group or a $C_6$-$C_{12}$ aryl group; and
$R^3$ represents hydrogen or methyl.

In certain embodiments, $R^2$ represents hydrogen.
In certain embodiments, $R^1$ represents hydrogen.
In certain embodiments, $R^3$ represents hydrogen.
In certain embodiments, Ar represents phenyl.
In certain embodiments, the epoxy resin moiety is derived from a resin selected from the group consisting of a novolac epoxy resin, a bisphenol A epoxy resin, a bisphenol F epoxy resin, an aliphatic epoxy resin, and a glycidyl amine resin.

In the illustrated example, the epoxy resin moiety is derived from a cresol-novolac epoxy resin.

The flame-retardant resin composition of the disclosure includes the phosphorous-containing compound and a resin.

In certain embodiments, the resin contained in the flame-retardant resin composition of the disclosure is a thermosetting resin.

The cured flame-retardant resin of the disclosure is obtained by curing the flame-retardant resin composition.

The method for preparing the phosphorous-containing compound of the disclosure includes the step of:

subjecting a p-hydroxy benzoyl derivative of Formula (II) and an oxa-phosphaphenanthrene oxide of Formula (III) to a reaction at a temperature ranging from 190 to 250° C. in the absence of a solvent, Formula (II)

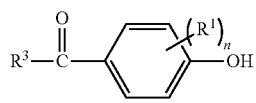

Formula (III)

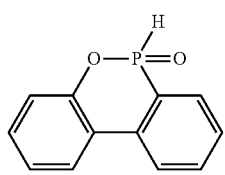

wherein n, $R^1$ and $R^3$ are the same as those defined for the phosphorous-containing compound represented by Formula (I), and a molar ratio of the p-hydroxy benzoyl derivative to the oxa-phosphaphenanthrene oxide ranges from 1:2 to 1:5.5.

In certain embodiments, the p-hydroxy benzoyl derivative of Formula (II) and the oxa-phosphaphenanthrene oxide of Formula (III) are subjected to to a reaction at a temperature ranging from 200 to 220° C.

The following examples are provided to illustrate the embodiments of the disclosure, and should not be construed as limiting the scope of the disclosure.

EXAMPLES

Synthesis of Phosphorous-Containing Compounds P1-P4

Synthesis Example 1

DOPO (630 g, 2.92 mol) was heated at 150° for 1 hour to remove water therefrom, followed by addition of 4-hydroxybenzaldehyde (70 g, 0.57 mol) thereinto to conduct a reaction at 200° C. under a nitrogen atmosphere for 3 hours to obtain a phosphorous-containing compound P1. The scheme for the reaction in Synthesis Example 1 is shown below.

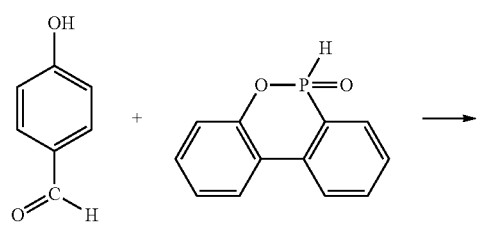

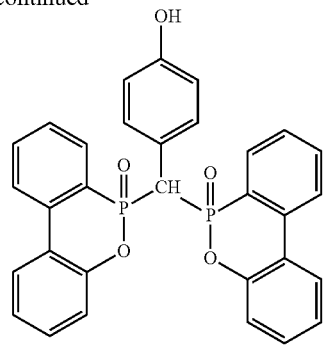

P1

Figure 1:
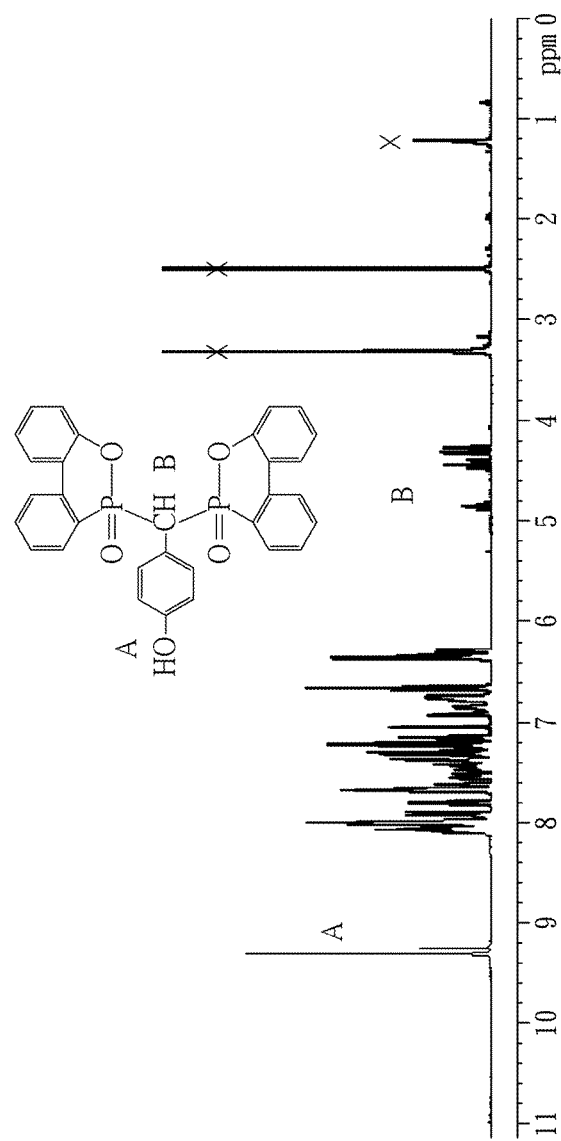
FIG. 1 is a $^1$H NMR spectrum of a phosphorous-containing compound P1 obtained in an illustrated example.
Figure 2:
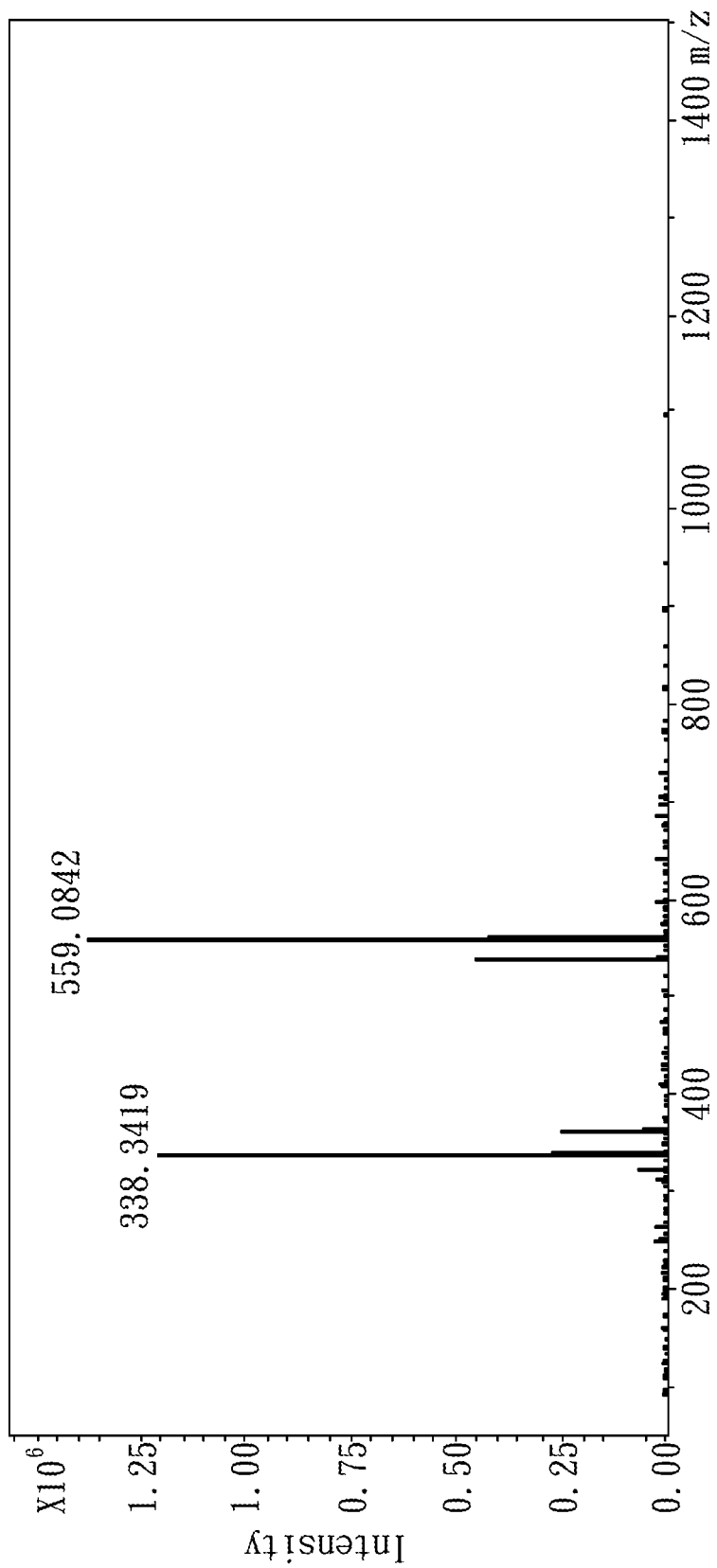
FIG. 2 is a mass spectrum of the phosphorous-containing compound P1.

As shown in the scheme, the phosphorous-containing compound P1 includes one phenyl group having a reactive group (i.e., OH) and two DOPO moieties. The phosphorous content of the phosphorous-containing compound P1 is 11.55 wt %. The $^1$H NMR spectrum and the mass spectrum of the phosphorous content of the phosphorous-containing compound P1 are shown in FIG. 1 and FIG. 2, respectively.

Synthesis Example 2

The phosphorous-containing compound P1 (53.6 g, 0.1 mole) and epichlorohydrin (170 g, 1.8 mol) were added into a reaction vessel, and were reacted under reflux for 6 hours to recover unreacted epichlorohydrin, followed by addition of toluene, water washing, and drying to obtain a phosphorous-containing compound P2. The scheme for the reaction in Synthesis Example 2 is shown below.

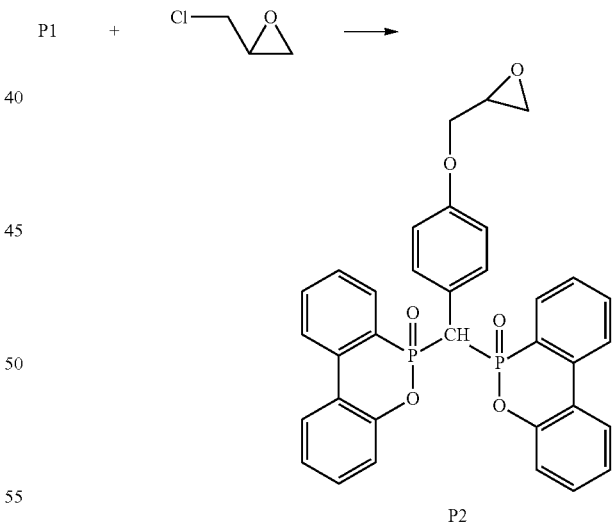

P2

As shown in the scheme, the phosphorous-containing compound P2 includes one phenyl group having a reactive group (i.e., an epoxy group) and two DOPO moieties.

Synthesis Example 3

The phosphorous-containing compound P1 (53.6 g, 0.1 mole), aniline (9.3 g, 0.1 mol), and para-formaldehyde (3.0 g, 0.1 mol) were added into a reaction vessel, and were reacted at 110° C. for 3 hours, followed by addition of chloroform (500 ml). An organic phase was collected after washing with an aqueous NaOH solution (1N) and pure water. A phosphorous-containing compound P3 was obtained after removing the solvent from the organic phase. The scheme for the reaction in Synthesis Example 3 is shown below.

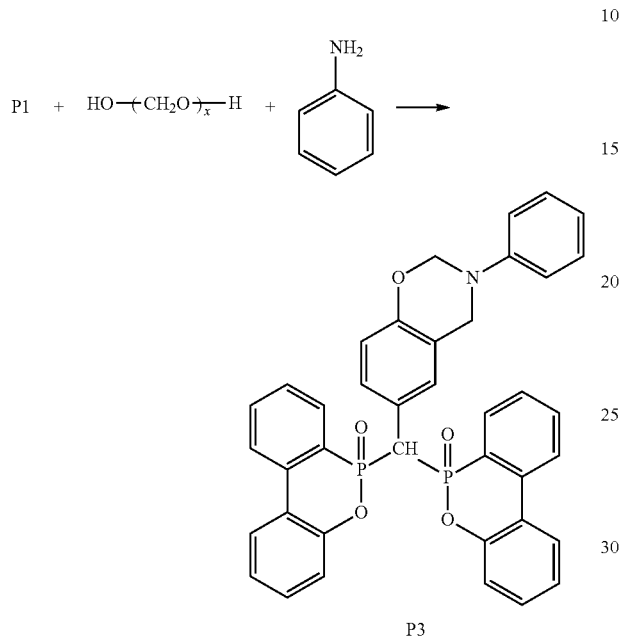

P3

As shown in the scheme, the phosphorous-containing compound P3 includes one benzoxazine group and two DOPO moieties.

Synthesis Example 4

The phosphorous-containing compound P1 (53.6 g, 0.1 mole) and a cresol-novolac epoxy resin (34 g, 1.8 mol) were dissolved into methyl isobutyl ketone (800 ml), followed by addition of triphenyl phosphine (0.6 g) and a reaction under reflux for 3 hours. A phosphorous-containing compound P4 was obtained after removing the solvent. The scheme for the reaction in Synthesis Example 4 is shown below.

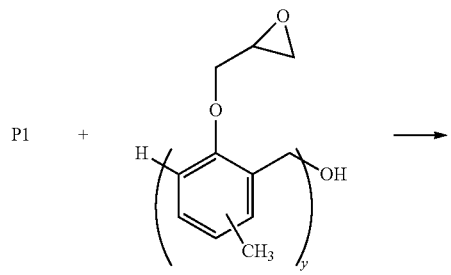

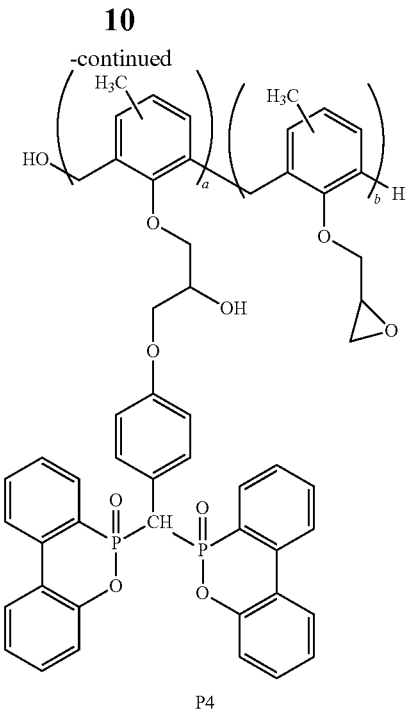

P4

As shown in the scheme, the phosphorous-containing compound P4 includes two DOPO moieties and one phenyl group linking an epoxy resin moiety.

Application Examples 1-4 and Comparative Application Example 1

Preparation of Flame-Retardant Resin Composition and Flame-Retardant Resin:

Diglycidyl of bisphenol A (DGEBA, epoxy equivalent: 188 g/mol), dicyanodiamide (DICY), and the phosphorous-containing compound P1 were formulated in methyl ethyl ketone using the amounts shown in Table 1 below to obtain flame-retardant resin compositions of Application Examples 1-4 and a resin composition of Comparative Application Example 1, each of which was cured by sequential heating at 160 for 1 hour, at 190° C. for 2 hours, and at 200° C. for 2 hours, thereby obtaining cured flame-retardant resins E1-E4 and cured resin CE. The phosphorous contents of the cured flame-retardant resins E1-E4 and the cured resin CE were respectively determined using elemental analysis. Td5 (degradation temperature at 5% weight loss) of each of the cured flame-retardant resins E1-E4 and the cured resin CE was determined using thermogravimetric analysis under atmosphere. The flammability rating of each of the cured flame-retardant resins E1-E4 and the cured resin CE was determined using a UL-94 flame rating test method. The results are shown in Table 1.

TABLE 1

| Resins | DGEBA (phr) | DICY (phr) | P1 (phr) | Phosphorous Contents (wt %) | Td (° C.) | Flammability Rating (UL 94) |
| --- | --- | --- | --- | --- | --- | --- |
| E1 | 100 | 7 | 5 | 0.52 | 321 | V1 |
| E2 | 100 | 7 | 10 | 0.99 | 317 | V0 |
| E3 | 100 | 7 | 15 | 1.42 | 312 | V0 |
| E4 | 100 | 7 | 20 | 1.82 | 320 | V0 |
| CE | 100 | 7 | 0 | 0 | 319 | Failed |

As shown in Table 1, the flame retardance of the cured flame-retardant resin may be enhanced by the phosphorous-containing compound of the disclosure while satisfactory thermal stability may be attained for the cured flame-retardant resin containing the phosphorous-containing compound of the disclosure.

In view of the aforesaid, the phosphorous-containing compound of the disclosure includes two DOPO moieties and one phenyl group having a reactive group and has relatively high phosphorous content. The flame retardance and the thermal stability of the cured resin may be enhanced by containing the phosphorous-containing compound of the disclosure therein.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A phosphorous-containing compound represented by Formula (I):

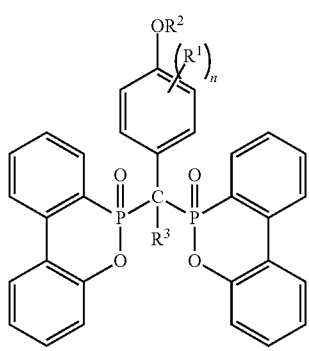

Formula (I)

wherein n is an integer ranging from 1 to 4;

$R^1$ represents hydrogen or a linear or branched $C_1$-$C_4$ alkyl group, and a plurality of $R^1$s are the same or different when n is larger than 1;

$R^2$ represents hydrogen,

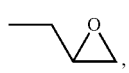

or

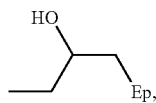

wherein Ep is an epoxy resin moiety; or

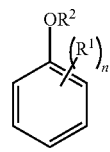

represents

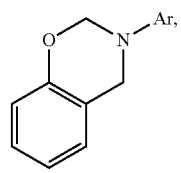

wherein Ar represents a linear or branched $C_1$-$C_{12}$ alkyl group or a $C_6$-$C_{12}$ aryl group; and $R^3$ represents hydrogen or methyl.

2. The phosphorous-containing compound according to claim 1, wherein $R^2$ represents hydrogen.

3. The phosphorous-containing compound according to claim 1, wherein $R^1$ represents hydrogen.

4. The phosphorous-containing compound according to claim 1, wherein $R^3$ represents hydrogen.

5. The phosphorous-containing compound according to claim 1, wherein Ar represents phenyl.

6. The phosphorous-containing compound according to claim 1, wherein said epoxy resin moiety is derived from a resin selected from the group consisting of a novolac epoxy resin, a bisphenol A epoxy resin, a bisphenol F epoxy resin, an aliphatic epoxy resin, and a glycidyl amine resin.

7. A flame-retardant resin composition, comprising the phosphorous-containing compound according to claim 1 and a resin.

8. A cured flame-retardant resin obtained by curing the flame-retardant resin composition according to claim 7.

9. A method for preparing the phosphorous-containing compound according to claim 1, comprising the step of:

subjecting a p-hydroxy benzoyl derivative of Formula (II) and an oxa-phosphaphenanthrene oxide of Formula (III) to a reaction at a temperature ranging from 190 to 250° C. in the absence of a solvent,

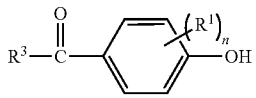

Formula (II)

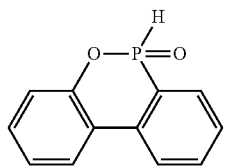
Formula (III)
wherein
n, $R^1$ and $R^3$ are the same as those defined in claim 1, and a molar ratio of the p-hydroxy benzoyl derivative to the oxa-phosphaphenanthrene oxide ranges from 1:2 to 1:5.5.
10. The method according to claim 9, wherein the temperature ranges from 200 to 220° C.
* * * * *